US00PP08333P

United States Patent [19]

Skirvin et al.

[11] Patent Number: Plant 8,333

[45] Date of Patent: Aug. 3, 1993

[54] BLACKBERRY PLANT NAMED ILLINI HARDY

[75] Inventors: Robert M. Skirvin, Champaign; Alan G. Otterbacher, Urbana, both of Ill.

[73] Assignee: Board of Trustees of the University of Illinois, Urbana, Ill.

[21] Appl. No.: 710,808

[22] Filed: Jun. 6, 1991

[51] Int. Cl.[5] ..... A01H 5/00

[52] U.S. Cl. ..... Plt./46.1

[58] Field of Search ..... Plt./46

[56] References Cited

U.S. PATENT DOCUMENTS

P.P. 6,679 3/1989 Moore ..... Plt. 46

*Primary Examiner*—James R. Feyrer

*Attorney, Agent, or Firm*—Yahwak & Associates

[57] ABSTRACT

A new and distinct variety of blackberry plant which exhibits erect thorny growth, is vigorous and hardy in cold climates. The plant produces fruits which are shiny black, medium sized, slightly acidic and flavorful.

5 Drawing Sheets

SUMMARY OF THE INVENTION

This invention concerns a new and distinct variety of blackberry which was made by a controlled cross between 'Chester Thornless'×NY 95 in the winter of 1979–80 at the University of Illinois, Urbana, Ill. 61801. While conventionally referred to as 'Illini Hardy', the plant may also be designated as Rubus 'Illini Hardy'. The seedling was field planted in 1980 and selected in 1983.

The invention has inter alia, the following characteristics:

1. this blackberry is the hardiest blackberry studied at Urbana, Ill., a site normally considered too cold for successfully growing blackberries. It also has performed successfully at Geneva, N.Y. It appears to be adapted to well drained sites with good air drainage from the USDA hardiness zones 5 to 8.

2. the canes of this blackberry are erect and have prominent prickles (thorny);

3. many of the mature canes are large in diameter (2 to 3 cm at 15 cm from the soil);

4. the fruits are shiny black, medium sized (avg wt=4.5 gms/berry), slightly acidic and flavorful.

BRIEF DESCRIPTION OF THE DRAWINGS

The accompanying drawings are color photographs showing typical specimens of the new variety in color as nearly true as is reasonably possible to make in a color illustration of this character.

DETAILED DESCRIPTION OF THE DISCLOSURE

The new invention described herein has been named 'Illini Hardy' blackberry.

Growing season: In Urbana, Ill., the invention blooms in May to produce a single crop of berries. The fruit ripens mid to late July. The ripening season of the plants according to the present invention is much more concentrated that its thornless parent 'Chester Thornless'.

Figure 3:
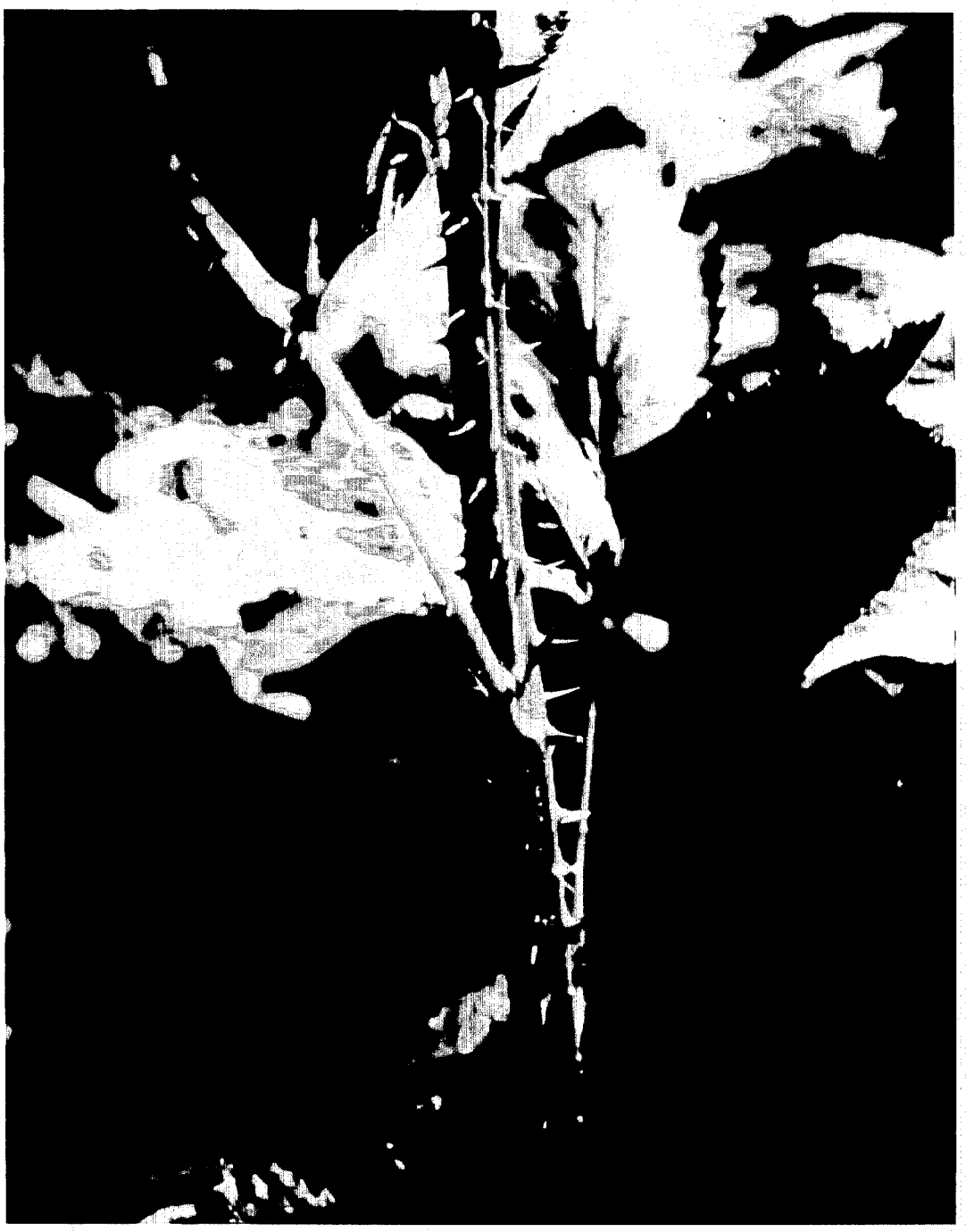
FIG. 3 shows a close-up taken of a young cane of a plant according to the present invention showing the thorn placement and structure.

Plant form: The growth habit of the invention is vigorous canes that are thorny and erect up to about 1.0 to 1.5 meters, after which they begin to arch. Suckering is limited, and the plant tends to grow as a clump of 6 to 10 canes. The plant produces most of its root suckers within 25 to 30 cm. of its base. Mature canes, grown in Urbana, Ill. and Geneva, N.Y., reached an average height of 1.5 to 2.0 meters. Canes of the invention branched sparsely to produce few laterals. Canes are thorny with straight to slightly curved prickles 5 to 10 mm long (FIG. 3).

Hardiness: The invention is the hardiest blackberry studied at Urbana, Ill., a site normally considered too cold for successfully growing blackberries. It has also performed successfully at Geneva, N.Y. The invention has sustained winter damage in the Minneapolis, Minn. ara. It appears to be adapted to well drained sites with good air drainage from USDA hardiness zones 5 to 8. In Illinois the invention has produced fruits annually since it first fruited in 1982. It has survived temperatures as low as −30° C. (−23° F.). In addition, the canes are thorny (covered with prickles) and are capable of producing flowering laterals from the basal 1 to 2 nodes of a floricane. Thus, even in years of severe winter kill, it is possible to produce some fruit.

Canes: The diameter of the canes, measured at 15 cm from soil level are:

*Floricane.*—1.6 cm (ranging from 1.2 to 2.1 cm).

*Immature primocane.*—1.35 cm (ranging from 1.0 to 2.0 cm).

*Mature primocane.*—1.9 cm (ranging from 1.5 to 2.3 cm).

*Internode length.*—5.9 cm (ranging from 5 to 6.7 cm).

With regard to the prickles, the color is green at the tip of the primocane. As they mature, they become pink-red at the base. They appear at a density of 1.7/cm (ranging from 1.2 to 2.3) along the primocane stem.

As the floricane matures, the mature canes become reddish brown. Utilizing Maerz, A. and M. Rea Paul, *A Dictionary of Color,* 1st edition, (1930), McGraw-Hill Book Company, New York, the color of the immature cane corresponds to plate 21:5L; the color of the cane in the sun side corresponds to plate 8.6C, and the color of the cane in the shade side corresponds to plate 21:7L.

The primocanes emerge beginning in the middle of May and continue to emerge through the month of July.

The branching height of the plants in pinched plants (i.e. plants that have had the apical meristem removed) is 43.3 cm (ranging from 27 to 53 cm). In non-pinched plants, the branching height is 48 cm (ranging from 44 to 52 cm).

Figure 1:
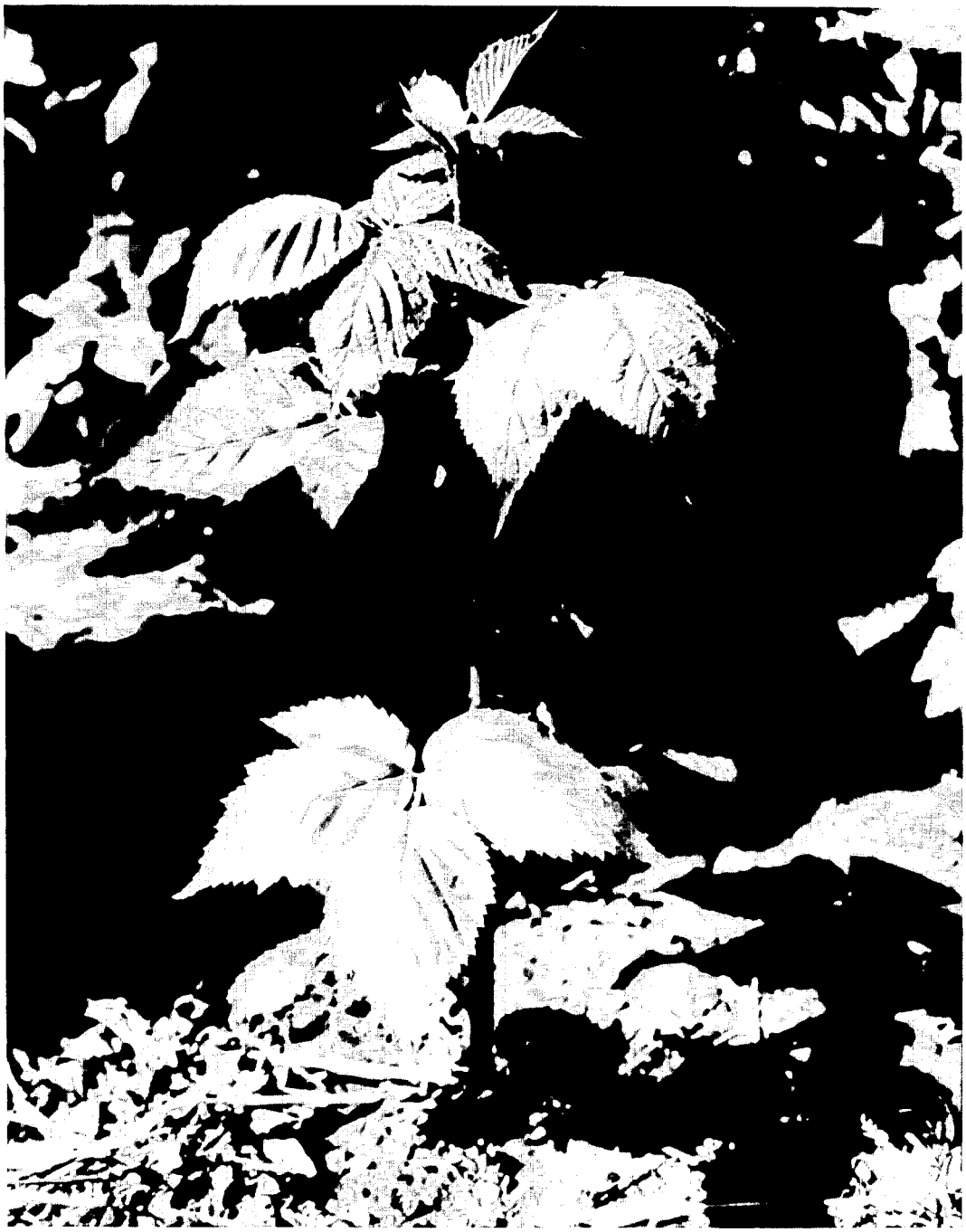
FIG. 1 shows the configuration of a young cane of the plant according to the present invention.
Figure 2:
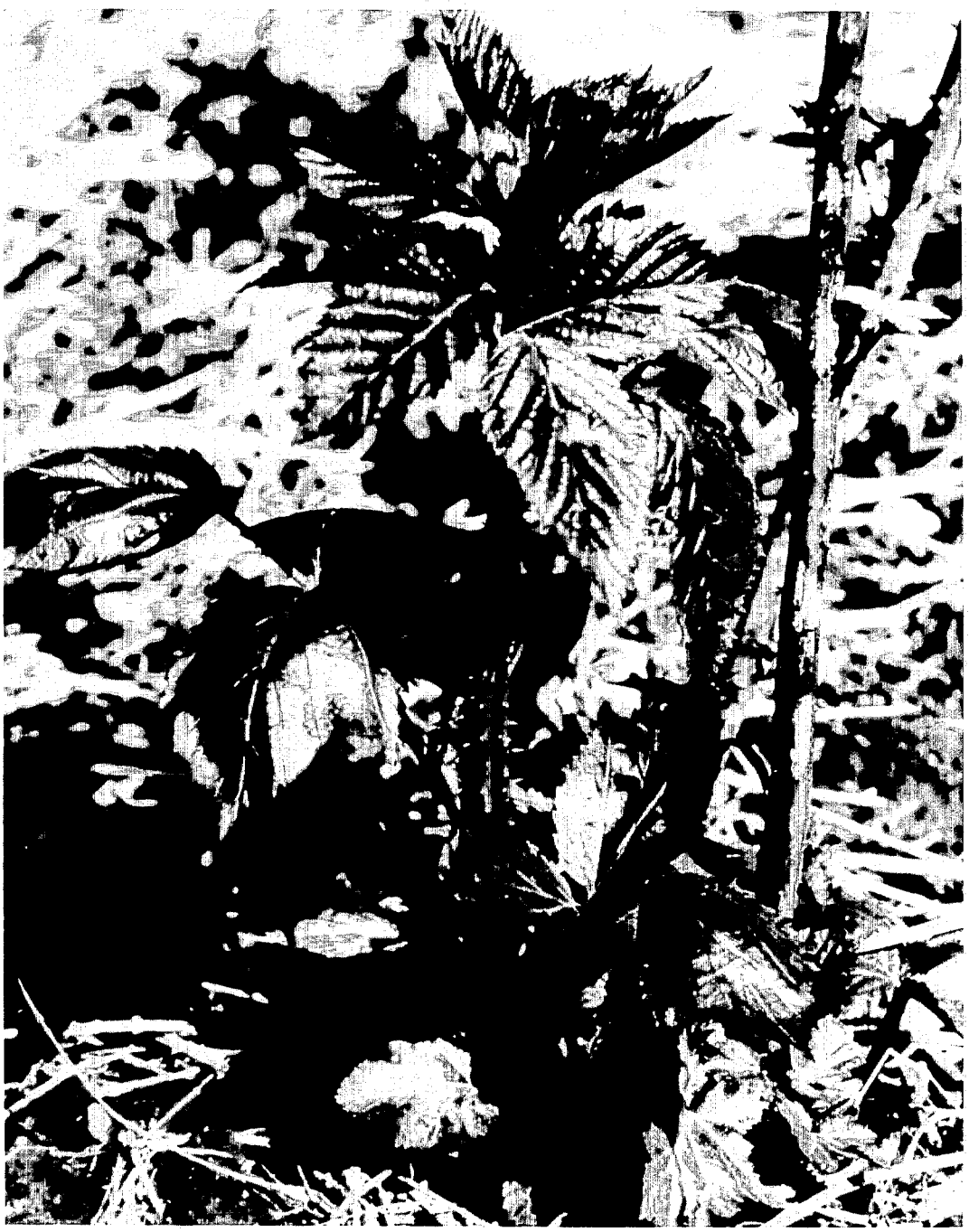
FIG. 2 shows the configuration of a young shoot of a plant according to the present invention growing alongside a mature cane of a previous year's growth.
Figure 4:
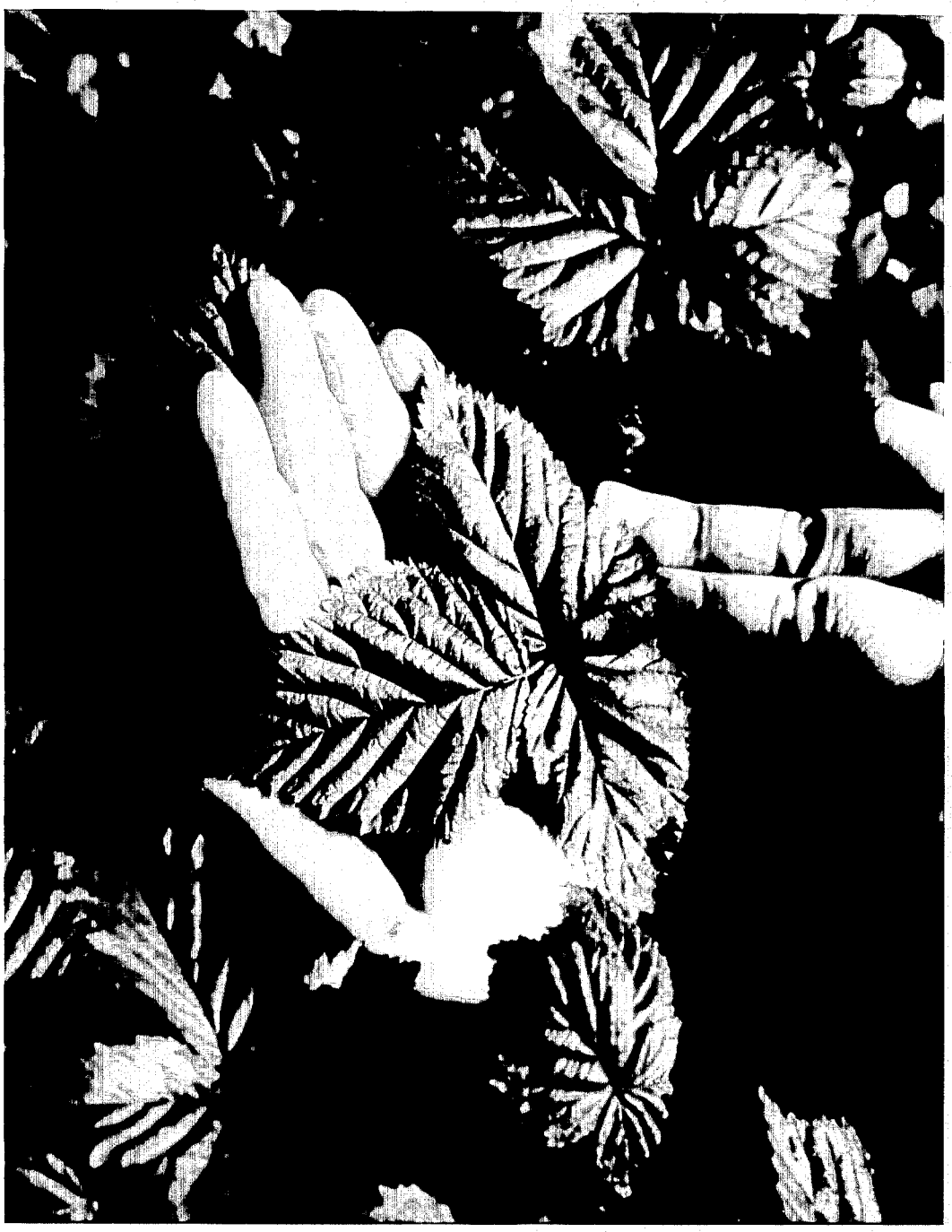
FIG. 4 shows the 3 leaflet leaf of a mature plant according to the present invention.

Foliage: The leaves of the Illini Hardy blackberry are (botanically) palmately compounded with 3 to 5 leaflets arranged alternately on the stem (FIGS. 1 and 4). The terminal leaflet is larger than the others. Leaflets are ovate with broadly acuminate tips. Stipules appear as 2 at the base of petiole; they are linear and up to 2 cm in length. The leaf margins are doubly serrate. Prickles appear on the petiole and lower half of the leaf midrib. They are green at the tip of primocane, but become pink-red at their base as they mature. Along the midrib and petiole, they appear at a density of 0.9/cm (ranging from 0.6 to 1.3 cm).

Pubescence may be considered hirsute. There is a greater density of pubescence on the underside of leaflets.

The petioles are green with some redness near the base; a redder coloration appears in those areas exposed to Sun.

Venation of the leaflets are pinate.

Figure 5:
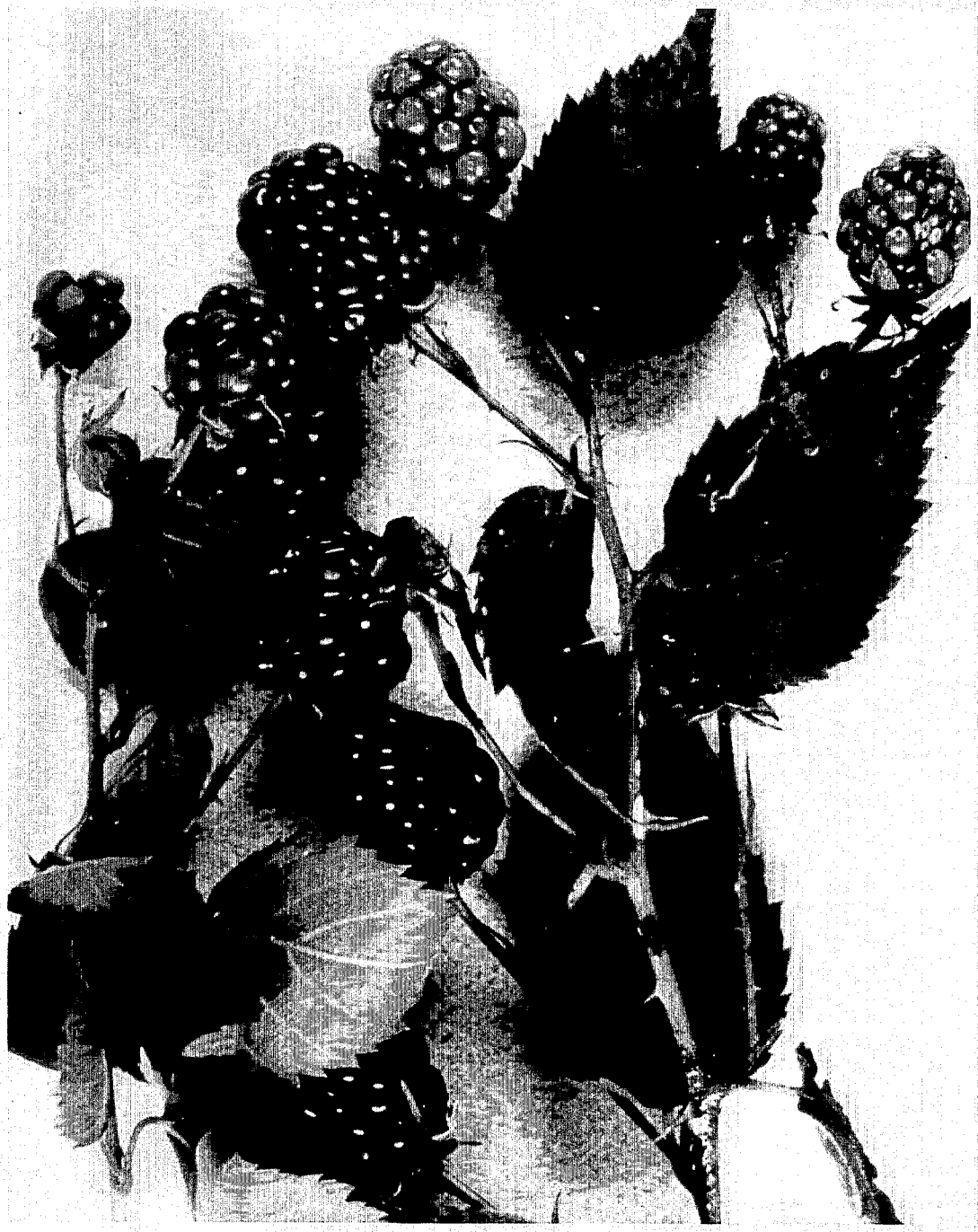
FIG. 5 shows the configuration and clustering of ripening berries only several of the berries having matured into glossy black berries.

From field observations, the primocanes appear as 3 to 5 leaflets (predominantly 5). The floricanes appear as 3 to 5 leaflets (predominantly 3); an occasional fused leaf (1 leaflet) is observed. The mature leaf diameter is 16.5 cm (ranging from 11.8 to 23.1 cm). The length of mature leaf (petiole and midrib) is 16.2 cm (ranging from 10.3 to 21.1 cm). Both the ribs and veins are prominently green. The color of the adaxial (upper surface) portion of the mature leaf is a medium green (Maerz, plate 24:4J); of the abaxial surface, the color is medium green (Maerz, plate 22:6L), however, the leaves are pubescent on the underside, giving the leaves a lighter green coloration; coloration in the immature (young, but fully expanded) leaf corresponds to Maerz, plate 23:8L for the adaxial surface, and plate 23:3L for the abaxial surface (FIG. 5).

The texture of the petioles is prickly. The petioles themselves have a length of 4.1 cm (ranging from 2.5 to 6.8 cm), and a red base that matches the color of the mature red stem.

Flowers: The flowers of the Illini Hardy blackberry have a blooming habit which is one in which the flowers bloom from apical blossoms downward. The date of first bloom in the general area surrounding Urbana, Ill. is in May, and produces a single crop of berries. The date of last bloom is about June 25th. The flowers are white and contain a branched cymose inflorescence. The florets number 10.1 cluster (ranging from 4 to 40 florets per cluster), and measure 3.1 cm (ranging from 2.6 to 3.2 cm) in diameter.

The petals of the blossom number 5 to 7, and appear as having uneven multiple dentations at the tips of the petals. They are slightly cupped (recurved), and white. The apical (king) blossom opens first.

The stamens number 112 (ranging from 1 to 134) and pollen is produced abundantly. There are no petaloid stamens. The sepals number 5 to 7. The pistils number 107 (ranging from 99 to 114).

Fruit: The fruit is characterized as having a ripening season more concentrated than that of 'Chester Thornless', one of the parents of the Illini Hardy blackberry. The average period of maturity is from about July 4th to August 10th in the area surrounding Urbana, Ill. The Illini Hardy blackberry plant produces an elliptically medium-sized fruit that is green (Maerz, plate 22:4L) red (Maerz, plate 6:10L) at immaturity and glossy black at maturity (FIG. 5); glossiness is retained even when the fruit is overripe. The fruit has an elliptical shape and weighs 4.6 grams (ranging from 4.1 to 5.0 grams). The diameter of the primary fruit at equator is 1.8 cm (ranging from 1.7 to 2.0 cm). The length of the primary fruit at the base pole is 2.2 cm (ranging from 1.9 to 2.5 cm). The length of the secondary fruit is the same as the primary fruit. The average length and width of the tertiary fruit is $1.73 \times 1.6$ cm. The skin of the fruit is medium firm.

The number of drupelets per berry average about 54.9, and are 4.0 mm (ranging from 3 to 5 mm) in size. The seed measures approximately $1.8 \times 2.9$ mm, and individual seed weighs approximately 3.5 mg. The color is tan to light green, and the shape is generally triangular.

The flavor of the fruit is acidic but flavorful, and resembles the flavor of wild blackberries more than either parent.

The fruit contains soluble solids of 10.1% (by refractometer), and has a pH of 2.52 (ranging from 2.5 to 2.53) [from composite expressed from 60 berries]. In preliminary yield trials, the invention has produced about 4,300 kilos per hectare (4,000 lbs per acre) of fruit per year.

Disease: To date, the invention has not had major pathological problems, and we do not know whether it is resistant to any major pathogens. However, it has shown some apparent resistance to Phytophora infection.

Having thus described and illustrated a new variety of blackberry plant what is claimed as new and desired to be secured by Letters Patent is set forth in the following claim:

1. A new and distinct cultivar of blackberry, substantially as described and illustrated, which is winter hardy throughout zones 5 to 8 of the United States and is characterized by erect prickly canes which produce shiny black ellipsoid berries.

* * * * *